United States Patent [19]
Remmers et al.

[11] Patent Number: 5,921,942
[45] Date of Patent: Jul. 13, 1999

[54] ADAPTIVELY CONTROLLED MANDIBULAR POSITIONING DEVICE AND METHOD OF USING THE DEVICE

[75] Inventors: John E. Remmers; Eric A. Hajduk; Ronald S. Platt, all of Calgary, Canada

[73] Assignee: University Technologies International, Inc., Canada

[21] Appl. No.: 08/738,342

[22] Filed: Oct. 25, 1996

Related U.S. Application Data

[60] Provisional application No. 60/007,155, Nov. 1, 1995.

[51] Int. Cl.$^6$ ....................................................... A61B 1/06
[52] U.S. Cl. ............................................. 600/529; 607/42
[58] Field of Search ..................................... 600/529, 534, 600/535, 536, 538, 595; 607/42

[56] References Cited

U.S. PATENT DOCUMENTS

| | | | |
|---|---|---|---|
| 4,765,340 | 8/1988 | Sakai et al. .............................. | 600/529 |
| 5,134,995 | 8/1992 | Gruenke et al. .................... | 128/204.23 |
| 5,199,424 | 4/1993 | Sullivan et al. .................... | 128/204.23 |

*Primary Examiner*—Robert L. Nasser
*Attorney, Agent, or Firm*—Burns, Doane, Swecker & Mathis LLP.

[57] ABSTRACT

The present invention relates to systems and methods for automatically and continuously regulating the amount of mandibular displacement to an optimal value during obstructive sleep apnea treatment. Obstructive sleep apnea therapy is implemented by a device which automatically reevaluates an applied mandibular displacement and continually searches for a minimum displacement required to adequately distend a patient's pharyngeal airway. The minimum optimal displacement varies with body position, stage of sleep throughout the night, the patient's body weight, and whether alcohol or sleeping medicine has been ingested.

22 Claims, 1 Drawing Sheet

ADAPTIVELY CONTROLLED MANDIBULAR POSITIONING DEVICE AND METHOD OF USING THE DEVICE

This application claims the benefit of U.S. Provisional Application No. 60/007,155, filed Nov. 1, 1995 and incorporates herein the disclosure of that application in its entirety.

FIELD OF THE INVENTION

The present invention relates generally to systems and methods for treating obstructive sleep apnea using an adaptive control system for adjusting and positioning a mandibular positioning device.

BACKGROUND OF THE INVENTION

Obstructive sleep apnea (OSA) is a common disorder which produces considerable morbidity and mortality. The disorder arises during sleep when the victim undergoes repeated cessation of breathing. This cessation results from an obstruction of the throat air passage (pharynx) due to severe narrowing or a collapse of the throat air passage. Repeated cessation of breathing reduces blood oxygen and disturbs sleep. Reduction in blood oxygen can cause hypertension, heart attacks and strokes. Additionally, sleep disturbances can produce excessive daytime sleepiness, headache, depression, irritability and cognitive impairments.

Medical research over the past decade has produced a standard approach to obstructive sleep apnea therapy, known as nasal continuous positive airway pressure (CPAP). In this therapeutic approach, a patient's nose is covered with a mask that forms a pressure seal with the surrounding face. While the patient sleeps, the mask is pressurized to a level that distends the collapsible throat air passage, thereby preventing obstruction.

This therapeutic approach provides two significant advantages: it is uniformly effective and it is entirely benign. A major disadvantage of this approach is that the patient must remain overnight in a hospital sleep center to undergo a full night polysomnography study with the pressure mask in place to determine the therapeutic level of pressure. A further disadvantage of this approach is that the pressure delivered to the patient during the polysomnography study is constant and fixed at the prescribed level, even though the patient's requirements may vary throughout the night and from night-to-night.

The overnight study presents a potential bottleneck to treating a high volume of patients with obstructive sleep apnea because it typically requires two full night polysomnographic studies for each new patient: one to establish the diagnosis (diagnostic-polysomnogram) and another to establish the aforementioned therapeutically optimal pressure (therapeutic-polysomnogram). The therapeutic polysomnographic study is necessary to determine the minimum level of pressure required to produce a patent pharyngeal airway (i.e., to determine the necessary therapeutic pressure required for properly treating the patient). These studies, performed in a specialized hospital sleep center, allow a specialist to specify the pressure to be used when prescribing nasal CPAP therapy. For this reason, the therapy cannot be prescribed by an internist or general practitioner.

Due to the requirement of two night polysomnographic studies, hospital sleep centers are crowded even though only a small percentage of obstructive sleep apnea victims are presently being treated. Further, the significant cost of the overnight polysomnographic study by a hospital sleep center represents a significant obstacle to diagnosing and treating the large population of sleep apneics. The backlog of undiagnosed and untreated obstructive sleep apnea patients thus represents a substantial public health problem.

To address the foregoing drawbacks of existing approaches to diagnosis and treatment of obstructive sleep apnea, recent commercial technology provides overnight, unattended monitoring of breathing in the patient's home. Such unattended monitoring generally permits the physician to diagnose obstructive sleep apnea without requiring a diagnostic overnight study in the hospital sleep center. However, a hospital sleep center is still required for establishing the therapeutically optimal pressure of nasal CPAP in each patient. Accordingly, medical practitioners have been slow to use the new monitoring technology for diagnostic purposes since the patient must, in any case, be referred to a sleep center for a full night therapeutic polysomnographic study.

While there is a continuing need for CPAP technologies, clinical studies and general clinical experience indicate that nasal CPAP is not always an effective treatment for many patients with obstructive sleep apnea, particularly those with symptoms of mild to moderate severity.

Various surgical approaches have been employed to correct the structural abnormality of the pharyngeal airway. Excluding massive reconstruction of the mandibular, maxilla and/or tongue, the only widely employed surgery has been uvulopalatopharyngoplasty (UPPP). However, results with UPPP are disappointing unless patients are selected by pharyngeal endoscopy during sleep and, even then, the long term benefits are questionable. Laser-assisted uvulopalatoplasty (LAUP) is a new approach which has been recommended for obstructive sleep apnea. No studies have reported the effectiveness of LAUP in the treatment of obstructive sleep apnea, but there is little reason to anticipate that it will be more effective than UPPP although it may be more convenient, less expensive and may prove to be a useful adjunct therapy to be used in combination with mandibular positioner (MP) therapy for patients in which MP therapy does not eliminate apneas and hypopneas.

Stationary oral appliances which draw the tongue forward have been used in the treatment of snoring. In addition, some recent studies suggest that a fixed oral appliance (i.e., mandibular positioner) which holds the lower jaw (i.e., mandible) of the patient forward as the patient sleeps is effective in treating obstructive sleep apnea, especially mild obstructive sleep apnea. Studies have shown that ventral displacement of the mandible enlarges the pharyngeal airway and acts to prevent its closure. Conventional mandibular positioners are constructed by a dentist or orthodontist at a fixed position for holding the mandible forward. The proper fixed position is determined through trial and error by having the patient try a series of mandibular positioning devices until the most effective one is found. Once the mandible displacement is set for the device, it remains stationary with no accommodation for variations in the obstructive sleep apnea, such as body position, sleep state, effects of drugs, and congestion of the patient.

An adjustable mandibular positioner, developed by Dr. A. Lowe, Head, Department of Orthodontics, University of British Columbia allows incremental adjustment of the ventral displacement of the mandible. This device is referred to as a screw adjustable mandibular positioner (SAMP), because its upper and lower full arch orthotics are connected by a manual screw device which is adjusted by the patient or dentist to set the magnitude of mandibular advancement.

Thus, the patient or dentist can progressively advance the mandible with the SAMP over a period of weeks to months so that mandibular muscles and ligaments can adjust, thereby allowing greater ventral displacement and minimizing side effects.

Accordingly, it would be desirable to render the therapy of obstructive sleep apnea more practical and convenient. To achieve this end, a method and system for automatically establishing the desired mandible advancement for a patient during changing sleep conditions is needed. More particularly, a system is needed with an adaptively controlled mandibular positioner that automatically adjusts to a patient's needs throughout the night and from night to night.

SUMMARY OF INVENTION

The present invention is therefore directed to providing a practical, convenient and cost-effective system for adaptively treating obstructive sleep apnea with an automatic, self-adjusting mandibular positioner. Further, the invention is directed to portable systems and methods for automatically and continuously regulating the position of the patient's mandible to an optimal position during obstructive sleep apnea treatment during long term nightly use at home. The present invention utilizes an automatic mandibular positioning system having adaptive control software which uses readily measurable, robust feedback variables to automatically adjust a mandibular positioner for obstructive sleep apnea treatment. Obstructive sleep apnea therapy is implemented in the present invention by automatically applying an appropriate mandible advancement to a patient. The mandible position is continuously reevaluated and optimized throughout the night. The optimal position varies with body position, congestion, stage of sleep, and whether any deleterious substances, such as alcohol or sleeping medicine, have been ingested.

The present invention is a portable adaptive control system which continually searches for the optimal minimum mandible advancement required to adequately distend a patient's nasal pharyngeal airway. By rendering the system portable, a large percentage of obstructive sleep apnea victims can be cost-effectively treated in their homes, thus reducing the overcrowding in expensive hospital sleep centers. Optimal minimum advancement is used because greater advancements increase the likelihood of side effects (e.g., sore muscles), and reduce the likelihood of patient compliance. A patient's compliance in regularly using the system is a significant concern inasmuch as the system is a portable device used at the patient's home without the supervision of a hospital sleep center specialist.

In one aspect of the present invention there is provided a method for adaptively controlling mandibular displacement for the treatment of obstructive sleep apnea in a patient by (a) monitoring the patient for evidence of obstruction of the patient's airway, (b) displacing the patient's mandible if evidence of obstruction is detected and (c) repeating steps (a) and (b) until evidence of obstruction is eliminated or reduced below a predetermined value.

In another aspect of the present invention there is provided a method for adaptively controlling mandibular displacement for the treatment of obstructive sleep apnea in a patient by detecting obstruction in a patient's upper airway system, identifying periods of inspiration and expiration for the patient, and incrementally adjusting a patient's mandible in response to the obstruction information detected during the period of inspiration.

In yet another aspect of the present invention there is provided a system for adaptively controlling mandibular displacement for the treatment of obstructive sleep apnea in a patient having an adjustable mandibular displacement device, a unit which detects evidence of obstruction of the patient's airway, and a control system for adaptively controlling the adjustable mandibular displacement device in response to the detecting unit.

BRIEF DESCRIPTION OF THE DRAWINGS

Other objects and advantages of the present invention will become more apparent from the following detailed description of preferred embodiments when read in conjunction with the accompanying drawings, wherein like elements have been designated by like numerals and wherein.

DETAILED DESCRIPTION OF THE PREFERRED EMBODIMENTS

The present invention is an auto-mandibular positioning (i.e., auto-MP) system for adaptively providing a mandible position effective in treating obstructive sleep apnea. The auto-MP system is an automatic, self-adjusting mandibular positioner and controller which performs detection, analysis, and decision-making functions.

Figure 1:
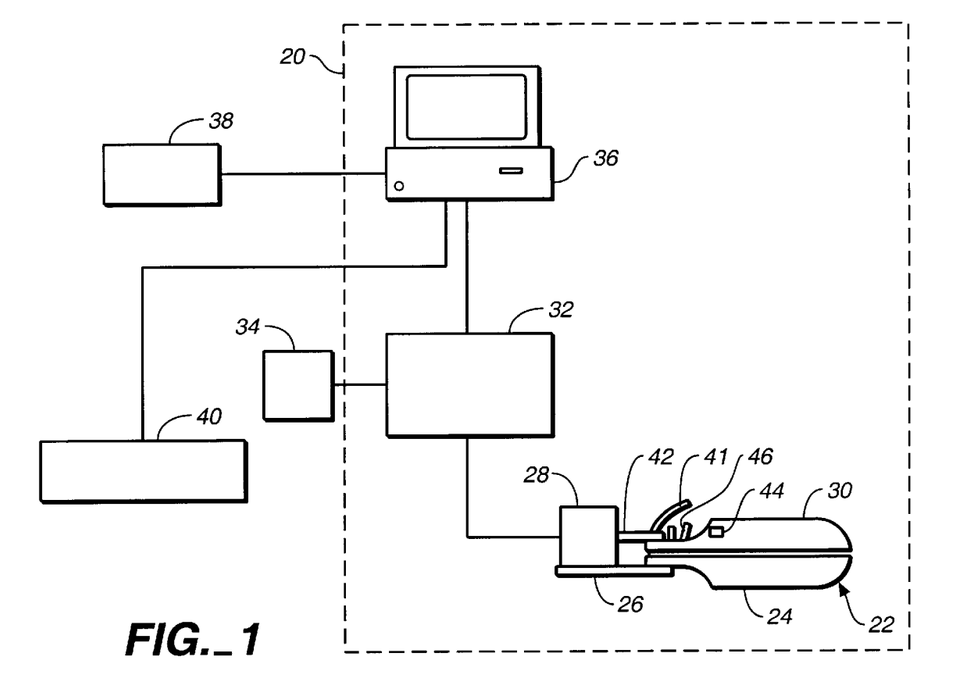
FIG. 1 is a diagrammatic representation of an adaptive mandibular positioner system.

With reference to FIG. 1, there is shown an adaptive mandibular positioner system 20 in accordance with one embodiment of the present invention. In this embodiment, adjustable mandibular displacement device 22 comprises a lower dental appliance 24 attached to mounting bracket 26 having a linear actuator 28 mounted thereon. Linear actuator 28 is in contact with or attached to upper dental appliance 30. The upper and lower dental appliances are free to slide relative to each other such that when the linear actuator 28 exerts force on the upper dental appliance (which can not move because the patient's upper teeth are attached to the maxilla which is fixed to the skull) the linear actuator 28, mounting bracket 26 and lower dental appliance 24 are displaced in a direction away from the patient. As a result, the lower dental appliance 24 draws the patient's mandible forward (i.e., ventrally) to open the patient's upper airway. In the illustrated embodiment, the actuator 28 and mounting bracket 26 displace the mandible in a linear manner, however it is within the scope of the invention that the actuator and mounting bracket be configured to displace the mandible along the patient's naturally occurring protruding path. For example, the path may be an arcuate path forward and downward, or forward and upward. Likewise, the patient's mandible may angle slightly to one side or the other as it protrudes.

In one embodiment, the upper and lower dental appliances are formed by filling an upper dental tray (which can be a partial or full arch) and a full arch lower dental tray, which can be custom fitted to a particular patient or be in standard sizes, for example small, medium and large, with a silastic impression material (e.g., PolyFil® TransBite available from SciCan® Medtech AG, Cham, Switzerland). Inserting the upper and lower dental trays in the patient's mouth and having the patient bite down until the molding material sets. In other embodiments, the upper and lower dental appliances can be formed with conventional materials such as heat deformable plastics which are placed in heated water or other suitable heating device before being inserted in the patient's mouth.

As illustrated in FIG. 1, the linear actuator 28 is driven by an actuator controller 32 having an external power source 34

(or an internal power source). Actuator controller 32 is controlled by adaptive control unit 36. The adaptive control unit in the illustrated embodiment is a personal computer but a special unit can be manufactured and used as well. Adaptive control unit 36 is usually located in an area near the patient and the mandibular positioning device 22. Attached to the adaptive control unit 36 is a recording and display device 38 (e.g., a polygraph paper chart and/or a magnetic recording device with a display) which receives inputs from the adaptive control unit 36 and from patient monitoring devices 40 (e.g., oxygen saturation, airflow, snoring sound) through the unit 36 as will be described in more detail below. The linear actuator 28 can be any of a variety of actuators as will be recognized by one of ordinary skill in the art and be within the scope of the present invention. Two of such actuators are described below. The linear actuator is capable of a maximum displacement of 25 millimeters, but for most patient's the maximum displacement is 16 millimeters.

In one such embodiment, the actuator system is comprised of a stepper motor controller connected to a personal computer for driving a stepper motor connected to a micrometer which moves a first hydraulic piston. The first hydraulic piston is in fluid communication through a 0.5 millimeter inside diameter, 2 millimeter outside diameter hydraulic line with a second hydraulic piston and cylinder mounted on the mounting bracket 26. The second hydraulic piston has a pressure plate for contacting or attaching to the upper dental appliance. When the stepper motor and micrometer move the first hydraulic piston, the pressure in the hydraulic line causes the second hydraulic piston to exert force on the patient's upper teeth through the pressure plate in contact with the upper dental appliance and protrude the patient's mandible with the lower dental appliance. When the pressure in the first hydraulic piston is reduced, the natural elastic nature of the patient's muscles in the jaw cause the patient's mandible to retrude while biasing members attached between the second hydraulic piston and the pressure plate cause the second hydraulic piston to retract. In this embodiment, moving the stepping motor 1 millimeter results in 1 millimeter of displacement of the patient's mandible. Optionally, a pressure transducer can be in fluid communication with the hydraulic line to measure the amount of force being exerted on the patient's muscles and ligaments to prevent excessive force that may cause patient discomfort or arousal. Preferably, the second piston and cylinder and mounting bracket are made of aluminum or similar lightweight material so that the patient is not aware of external forces applied to the patient's teeth.

In another embodiment of the actuator system, the hydraulic system just described is replaced with a small stepper motor (e.g., model no. 20841-05 available from Haydon Switch and Instrument, Inc. in Waterbury, Conn.) mounted on the mounting bracket 26. The actuator controller 32 is a model 40105 Bipolar Chopper Driver available from Haydon Switch and Instrument, Inc. in Waterbury, Conn. The stepper motor mounted on the mounting bracket 26 has a screw shaft extending through the center thereof with a pressure plate at the distal end of the shaft for contacting or attaching to the upper dental appliance. When the actuator controller 32 receives a protrude signal from the adaptive control unit 36, the actuator controller sends a signal to the stepper motor which rotates the screw shaft. The screw shaft extends toward the upper dental appliance to exert force on the patient's upper teeth through the pressure plate in contact with the upper dental appliance and protrude the patient's mandible with the lower dental appliance. When the actuator controller 32 receives a retract signal from the adaptive control unit, the actuator controller sends a signal to the stepper motor which rotates the screw shaft in the opposite direction. The screw shaft retracts the pressure plate and the natural elastic nature of the patient's muscles in the jaw cause the patient's mandible to retrude. In this embodiment, the adaptive control unit sends three signals to the actuator controller. One signal tells the stepping motor to turn on or off, another signal tells the stepping motor the direction to move (i.e., clockwise or counterclockwise), and another signal tells the stepping motor the number of steps to move (e.g., 1 step=15 degrees of shaft rotation=$\frac{1}{40}$ millimeter of linear displacement).

Attached to the strut 42 of the linear actuator 28 are two cannulae 41 with openings positioned to correspond to the patient's nares (not shown) (FIG. 1). These cannulae are connected to a pressure transducer (e.g., Oyster model 723 from Schaller) for recording an index of respiratory airflow. The kinetic energy of the expired air increases the pressure in the cannula, thereby providing a direct index of expiratory airflow rate. Conversely, during inspiration, the pressure in the cannula decreases providing an index of inspiratory airflow. Snoring is sensed by a piezo-electric transducer applied to the neck over the trachea, typically using a contact microphone. Alternatively, the piezo-electric transducer can be implanted in the upper dental appliance. The signal from the transducer is digitized and integrated. Peak snoring and duration of snoring are detected. Snoring is deemed "detected" when a sound of 200 milliseconds duration is detected for 2 consecutive breaths. Arterial oxygen saturation is detected by a pulse oximeter attached to the ear lobe, the finger or the lip. For the lip, the light emitter 44 is attached to the ventral aspect of the upper dental appliance and the sensor 46 is attached to the strut of the upper dental appliance.

Feedback variables which provide the most useful information for the adaptive control system include: snoring sound, oxygen saturation and nasal airflow. These are selected because they are robust signals and are easily incorporated into the auto MP nightly use.

As snoring is caused by vibration of the soft palate, it is therefore indicative of an unstable airway and is a warning signal of the imminence of upper airway obstruction in patients that suffer obstructive sleep apnea. Snoring is itself undesirable not only as it is a disturbance to others but it is strongly believed to be connected with hypertension. If the resultant increase in mandibular protrusion is sufficient to completely stabilize the airway, snoring will cease. If a further snoring sound is detected, the protruded distance is again incrementally increased. This process is repeated until the upper airway is stabilized and snoring ceases. Hence, the occurrence of obstructive apnea can be eliminated by application of minimum mandible displacement at the time of use.

The adaptive control unit gradually decreases the mandible displacement if an extended period of unobstructed breathing occurs in order to ensure that the degree of mandible displacement is maintained at a level as low as practicable to prevent the onset of apnea. If, however, evidence of obstruction is detected by the adaptive control unit, the system will again act to incrementally increase the protruded distance of the mandible.

In use, a patient using adaptive mandibular positioner system 20 may connect himself to the apparatus and go to sleep. The mandible displacement is initially at a minimum displacement, for example, the patient's natural mandible position at rest or slightly protruded so as not to cause discomfort that prevents sleep. Not until some time after going to sleep and the patient's body relaxes will the airway start to become unstable and the patient will begin to snore or experience some obstruction of the airway. The patient inputs 40 will detect the snore or obstruction and send a signal to adaptive control unit 36. The adaptive control unit will then respond to the obstruction via the actuator controller 32 to increase the protruded distance of the patient's mandible. The displacement can be increased relatively rapidly, if the patient's condition so requires but care is taken to not arouse the patient.

If in the early stages of sleep some lesser mandible displacement will suffice, system 20 will not increase the displacement until needed, that is, unless the airway becomes unstable and evidence of obstruction commences, no increase in displacement is made. By continuously decreasing the displacement (unless the mandible is already in the natural position) in the absence of evidence of obstruction, the displacement is never substantially greater than that required to prevent apnea.

The adaptive mandibular positioner system 20 provides a system which adjusts mandibular displacement according to variations in a patient's breathing requirements throughout an entire sleep period. Further, system 20 will likewise accommodate variable displacement requirements owing to general improvements or deteriorations in a patient's general physical condition as may occur over an extended period of time.

Patient inputs 40 preferably comprise at least one of an oxygen saturation monitor, a sound monitor, and an airflow monitor which continuously detects changes in the patient's breathing patterns. Concurrently, the patient inputs unit 40 generates output signals corresponding to the continuously detected signals and transmits these signals to adaptive control unit 36.

Depending upon the characteristics of the patient inputs signal, the adaptive control unit may generate a command signal to either increase or decrease the mandibular displacement. The adjustable mandibular positioner 22, patient inputs 40 and adaptive control unit 36 thus comprise a feedback circuit or system capable of continuously and automatically controlling the displacement of the patient's mandible responsive to the patient's respiratory requirements as dictated by the patient's breathing patterns.

Obstruction of the upper airway is manifested by high upper airway resistance, hypopneas or apneas. High upper airway resistance is detected when snoring is present, peak flow is reduced and/or the profile of inspiratory flow is flat. Hypopneas are signified by snoring, reduction of peak airflow, flat inspiratory flow trajectory and a decrease in oxygen saturation. Apneas are manifested by absence of snoring and airflow followed by oxygen desaturation in the range of 5 to 10 seconds.

When the patient inputs unit 40 detects breathing patterns indicative of obstructed breathing, it transmits signals corresponding to this condition to the adaptive control unit 36. The adaptive control unit 36 then causes the mandibular positioner 22 to increase the protrusion of the mandible incrementally (e.g., in the range of 0.25 to 2 millimeters, preferably in the range of 0.5 to 1 millimeter) which opens the patients airway until obstructed breathing is no longer detected. The system also includes means such as appropriate logic programmed into the unit 36 whereby the displacement is gradually decreased if unobstructed breathing patterns are detected over a preselected period of time (e.g., in the range of 10 seconds to 4 minutes, preferably for 2 to 4 minutes). This feature serves to provide the patient with a ventral displacement of the mandible minimally sufficient to maintain airway patency during unobstructed breathing, thus enhancing patient comfort and therapy compliance.

Several embodiments for adaptive control of the auto MP are available. One embodiment utilizes a predetermined displacement step in position of the mandible during the expiratory phase. Snoring (if present) and peak airflow during a first test set (e.g., in the range of 1 breath to 10 breaths) after the displacement step are compared to the mean of the preceding breaths (e.g., in the range of 2 to 10 breaths, preferably 3 to 5 breaths). In addition, measures of the shape of the inspiratory flow profile (i.e., flatness and roundness) are calculated and compared to preceding values.

Another embodiment utilizes a strategy of incrementing the mandibular position by 1 millimeter when snoring and/or desaturations are present. After each increment, the feedback variables will be monitored for a predetermined period (e.g., in the range of 10 seconds to 4 minutes). Our studies indicate that often snoring will disappear shortly after the increment in mandibular position and then reappear. Accordingly, if snoring and desaturations reappear, the process will be continued until snoring reaches a minimum value and desaturations are eliminated, or the limits of extension are reached as indicated by pressure and displacement information.

In one embodiment, airflow is used to assess the respiratory and dynamic mechanical characteristics of a patient's pharyngeal airway (PA) during sleep and to adjust the therapeutic mandible advancement as required.

Respiratory airflow typically corresponds to patient breathing and has two sequential, tidal components: one caused by inhalation and another caused by exhalation. This tidal airflow is phasic and therefore allows the onset of inspiration and the onset of expiration to be identified. Because the onset and termination of inspiration are identifiable, parameters related to the shape of a time profile of inspiratory flow can also be determined. In a preferred embodiment, a degree of roundness and flatness of the inspiratory profile are determined as will be described later.

The measurement of airflow and subsequent determination of an inspiratory airflow profile are used to control the position of the patient's mandible in accordance with the present invention. When the degree of mandible displacement produces the maximal distention of the airway with the minimum displacement is abruptly reduced in sleeping patients suffering from obstructive sleep apnea, the pharynx is observed to collapse and the pharyngeal resistance increases accordingly. This change in upper airway resistance induces changes in peak inspiratory airflow and profile shape with little change in airway pressure below the obstruction. Accordingly, changes in airflow resistance can be inferred from changes in the inspiratory airflow.

Further retrusion of the mandible leads to progressive collapse of the pharyngeal airway which severely reduces inspiratory airflow and causes flow limitations (i.e., increased airflow resistance). Similarly, progressive increases in the degree of mandible protrusion leads to smaller decrements in airflow resistance as the pharynx widens and reaches the limits of its distensibility. The collapsible behavior of the pharyngeal airway in response to progressive reductions in the degree of mandible displacement provides a framework for determining an optimal therapeutic mandible displacement in accordance with the present invention.

Accordingly, a preferred embodiment includes an adaptive control system for displacing the patient's mandible in response to detected airflow. This mandible displacement is adaptively adjusted to apply an optimal minimum therapeutic displacement.

During a testing mode of the auto-MP system, the displacement of the patient's mandible is changed frequently. The position of the mandible is changed by sending a signal from the computer 36 to controller 32 which sends the proper signal to actuator 28.

Generally speaking, the adaptive control system generates an optimal desired (i.e., command) displacement by detecting airflow data over a predetermined period of time, identifying periods of inspiration and expiration, and extracting information or features from the airflow data. Using this information, the adaptive control system identifies a critical displacement ($D_{crit}$) at which a significant obstruction occurs during inspiration. More particularly, $D_{crit}$ corresponds to a lower limit of mandibular displacement associated with a significant decrease in peak inspiratory airflow and/or significant (i.e., critical) airflow limitation. After determining $D_{crit}$, the adaptive control system identifies an optimum (i.e., minimum) effective mandible position ($D_{opt}$) for eliminating the obstruction during inspiration.

The adaptive control system identifies $D_{crit}$ and decides upon $D_{opt}$ using a series of test displacements in the mandible position. Results of the tests are evaluated by examining inspiratory airflow. $D_{opt}$ is continuously updated during testing periods which are initiated throughout the night to account for changes in the patient's sleep stages and sleeping position.

Because a testing period is used to update $D_{opt}$, the adaptive control system also decides when to test the pharyngeal airway, and when to continue or to stop testing. Further, the adaptive control system (1) manages overall operation to optimize its own performance, and (2) monitors potential airflow measurement errors to accurately measure upper airway performance as will be described below.

Airflow changes and airflow profile changes in the upper airway system have been determined to be directly related to intra-pharyngeal pressure. By determining upper and lower limits of pharyngeal resistance from changes in airflow during a testing period, $D_{opt}$ can be determined for any patient at any time. Accordingly, the adaptive control system searches for $D_{opt}$ between a lower airflow limitation ($D_{crit}$) and an upper limit (full distention of the airway).

Operating within these relative limits ensures reliable assessment of the pharyngeal airway and an accurate determination of $D_{opt}$. Because airflow varies widely among patients and, for any particular patient, varies with sleep stage, $D_{opt}$ can not be determined by comparing airflow measurements with ideal or predicted standards.

Figure 2:
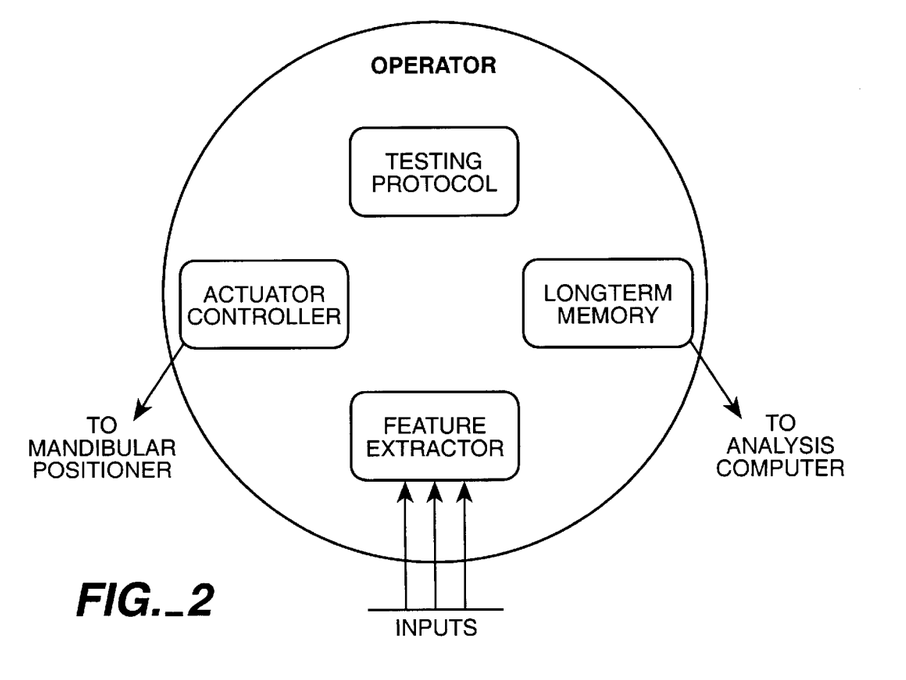
FIG. 2 is a conceptual diagram of an operator of the adaptive control system.

Generally speaking the adaptive control system conceptually includes four basic components for performing the aforementioned testing and non-testing control. As shown in FIG. 2, these four basic components are an operator, a feature extractor, a testing protocol, and long term memory.

a. Operator

The adaptive control operator is an overseer that has access to information of the feature extractor at all times, decides when and when not to enter the testing protocol, controls the flow of information to and from longterm memory, and maintains optimal performance and reliability. Decisions are made by the operator to ensure that the adaptive control system operates within predetermined operating limits so that accuracy is maintained.

The normal operating limits for the adaptive control system are based on rules of operation. These rules of operation ensure that so called performance indices are within predetermined physiological ranges, and that a respiratory phase threshold detection mechanism system is functioning efficiently. Further, these rules are used by the adaptive control system to make decisions, such as when to exit a testing period or when to return to a testing period.

To ensure operation within predetermined physiological limits, the rules are designed to have the adaptive control system operate whenever there is (1) a low to moderate level of variation in respiratory features, (2) no hypoventilation and (3) no apnea.

For purposes of the present discussion of preferred embodiments, a large variation in the respiratory features is defined as a variation coefficient value of 0.3 or more for four or more specified features (e.g., time of inspiration ($T_i$), total time of breath ($T_{tot}$), mean inspiratory airflow ($V_m$), peak inspiratory airflow ($V_p$), and Roundness) for a set of 2 to 40 breaths depending on whether it is in a testing or a non-testing mode, respectively; hypoventilation is defined as five (5) consecutive breaths with $V_m$ less than 40 percent of the predicted awake supine $V_m$; and apnea is defined as a 10 seconds duration of no change in respiratory phase.

Satisfaction of these rules is the criteria used by the adaptive controller in deciding whether or not to enter a testing mode. If these rules are not satisfied during a non-testing period, either a subsequent testing period is delayed or the adjustable mandibular positioner is adjusted or both. If these rules are not satisfied during a testing period, the testing ceases and there is a return to the previous $D_{opt}$, or to a displacement position previously set by an outside source, whatever is higher.

As mentioned above, the operator is an overseer which decides when to enter a testing mode. Decisions made by the adaptive control system (e.g., when to test and when to discontinue testing) are based on dynamic characteristics, or performance indices, of the pharyngeal airway during the non-testing and testing periods. During non-testing and testing periods, the adaptive control system continuously monitors breathing variations, hypoventilation, and apnea.

(1) Non-Testing Mode Periods

The adaptive control system operates in one of two basic modes: a non-testing mode (n-TM) and a testing mode (TM). Throughout the testing and non-testing modes, characteristics of the upper airway are continuously detected and evaluated by the feature extractor. In the non-testing mode (i.e., non-testing period), results generated by the feature extractor are used to determine if and when to delay testing, to optimize rules of operation, and to identify deteriorating changes in airflow.

While in the non-testing mode, the auto-MP system monitors the information from the feature extractor. This information is used to determine the presence of large variations in breathing frequency, hypoventilation, or apnea. Testing under these conditions could lead to erroneous results. Therefore entering into the testing mode may be delayed.

(2) Testing Mode Periods

When the adaptive control operator decides to redetermine $D_{crit}$ and $D_{opt}$, then the testing mode is executed in accordance with the testing protocol. As in a non-testing period, the operator has continuous access to the information from the feature extractor during a testing period to determine if it should continue to test for $D_{crit}$ and $D_{opt}$.

When the auto-MP system enters the testing mode, a specific testing protocol of incremental mandible displacements is followed. Prior to identifying $D_{opt}$, the testing protocol is only interrupted if a large breathing variation, an apnea or hypoventilation is detected. The results from the non-testing mode and the testing mode are retained in the longterm memory.

b. Feature Extractor

The feature extractor (FE) is the center for continuous acquisition and analysis of data. For example, the feature extractor generates performance indices in response to respiratory airflow data. These performance indices are a measure of the pharyngeal airway's dynamic state and are used by the operator for decision making in both the testing and non-testing modes. In alternate embodiments, additional signals (e.g., monitoring signals related to oxygen saturation and sound) can be input to the feature extractor to assist in the continuous sensing of dynamic characteristics of the pharyngeal airway.

The feature extractor has two basic functional modules: a data acquisition module and a respiratory cycle analysis (RCA) module. Data acquisition of the input signals (e.g., airflow) occurs via the patient inputs 40 every 8 msec. These values are then passed into an RCA module where eight consecutive values are averaged to produce a single low pass filtered average value every 64 msec. Each 64 msec average value is then continuously analyzed in the RCA module for phase of respiration, apnea, and breath features.

Performance indices generated by the RCA module are updated continuously as follows, where the asterisks indicate a real time occurrence of an update for the feature listed:

|  | During Inspiration | During Expiration |
|---|---|---|
| Respiratory phase | * | * (continually) |
| End of Breath |  | * (end of expiration) |
| RCA Abnormalities | * | * |
| Apnea | * | * |
| Breath Features: |  |  |
| $T_i$ |  | * (time of inspiration) |
| $T_e$ | * |  (time of expiration) |
| $T_{tot}$ |  | * (total time of breath) |
| $Vol_i$ |  | * (inspiratory volume) |
| $Vol_e$ | * |  (expiratory volume) |
| $V_m$ |  | * (mean inspiratory airflow) |
| $V_p$ |  | * (peak inspiratory airflow) |
| Flatness |  | * (measure of inspiratory flatness) |
| Roundness |  | * (measure of inspiratory roundness) |

As mentioned previously, an optimum mandibular position is determined by evaluating the effects of incremental protruded steps on inspiratory airflow. Accordingly, the RCA module is designed to continuously report breath changes in upper airway state (i.e., to identify respiratory phase and end of breath conditions based on extracted features). A breath is defined as an inspiratory period followed by an expiration period. Therefore, an end of breath condition is updated at the end of expiration.

When the RCA module detects a problem, then an RCA abnormalities condition is set. For example, the RCA module is designed to continuously report detection of apneas based on extracted features.

The breath features listed above are the dynamic physiological characteristics of the pharyngeal airway. Their variation, especially in combination, are excellent measures of the pharyngeal airway behavior. Values of $T_i$, $T_e$, $T_{tot}$, $Vol_i$, $Vol_e$, $V_m$ and $V_p$ (defined in the above table) are physiologically self explanatory breath features. Flatness and roundness values are breath features which are developed as measures of inspiratory airflow. The flatness and roundness values are used in accordance with preferred embodiments to identify pharyngeal airway behavior.

For purposes of the present discussion, flatness is defined as the relative deviation of the observed airflow from the mean airflow. In a preferred embodiment, individual values of airflow are obtained between 40% and 80% of the inspiration period. The mean value is calculated and subtracted from the individual values of inspiration flow. These individual differences are squared and divided by the total number of observations minus one. The square root of this product is used to determine a relative variation.

The relative variation is divided by the $V_m$ to give a relative deviation or a coefficient of variation for that breath. This measure of airflow therefore represents a measure of flatness over the mid-range of inspiration. A relatively low value is used to indicate that inspiration airflow during mid-inspiration is relatively constant. The common cause of this is flow-limitation secondary to pharyngeal collapse. Thus, a low value indicates the need for greater mandible protrusion.

For purposes of the present discussion, the roundness feature supplies information regarding the similarity between the normalized inspiration flow profile and a sine wave normalized for observed inspiration time and for observed peak flow. The airflow predicted from the sine wave, Vsine, is calculated from the following normalized sine wave equation:

$$Vsine = Vpeak * sine(F * \pi)$$

where Vpeak is observed peak flow and F equals the fraction of inspiratory time elapsed. This equation for predicting sequential airflow measurements is used when the ratio of peak flow to $T_i$ is less than 1.1 and greater than 0.45. For values of the ratio greater than 1.1 the peak is estimated by multiplying $T_i$ by 1.1, and for values below 0.45 the peak is estimated by multiplying $T_i$ by 0.45.

The differences between consecutive values of observed inspiratory airflow and that calculated from the sine wave equation value are squared and summed, and then divided by the total number of points. The square root of this product is then divided by the mean value of airflow for that inspiration to give a normalized value for that breath.

Accordingly, the roundness index provides an estimate of the degree to which the inspiration airflow profile resembles a sine wave. As flow limitation occurs or as the airflow signal becomes less sinusoidal, the roundness feature becomes larger. This indicates an increase in upper airway resistance and suggests that the protrusion of the mandible may not be adequate. $V_p$ and flatness are measures of flow limitation and roundness is a measure of increasing upper airway resistance.

To update the performance indices and other information presented in the above chart, the RCA module includes a respiratory phase threshold detection mechanism (TDM). The threshold detection mechanism detects the inspiration and expiratory phase changes in airflow. The accuracy of the feature extraction is very dependent upon accurate detection of the start of inspiration. In accordance with preferred embodiments, the start of inspiration is ascertained solely from airflow.

Basic assumptions in the threshold detection mechanism are that inspiration and expiratory volumes are approximately equal. Two factors affect the volumes causing them to be unequal. The volume of oxygen consumed per unit time is normally greater than the volume of carbon dioxide that is produced by the body. Further, breath-to-breath variation in tidal volume and timing during sleep, as well as arousal which alters alveolar ventilation and exact expiration volume, can result in a variation between inspiration and expiratory volumes.

Normally the inspiration tidal volume is 4% greater than the expiratory tidal volume. Over a 30 second period of quiet breathing, all variations can be approximately averaged out of this ratio. Therefore, a resultant average respiratory flow can be used as a basis to estimate the beginning of inspiration and to approximate non-respiratory flow. The actual start of inspiration flow can be detected when the airflow signal crosses a no-flow value. This is because the actual zero respiratory flow corresponds to the zero flow value.

c. Testing Protocol

During testing periods, the adaptive control system first reduces the protruded distance of the mandible and determines $D_{crit}$. This constitutes a characteristic lower limit for the ventral displacement of the mandible for a given state of the patient's pharyngeal airway (e.g., sleep stage, position, and so forth). Having established this lower limit, the optimum displacement value $D_{opt}$ is determined by progressively increasing the protruded distance. The increases in peak inspiration flow and changes in the shape of the inspiration airflow profile are recorded and used to identify $D_{opt}$.

The determination of $D_{crit}$ during a testing period is termed the $D_{crit}$ search. The subsequent determination of $D_{opt}$ during a testing period is termed the $D_{opt}$ search. Each search consists of a progressive series of incremental changes in mandible displacement (i.e., step decreases for $D_{crit}$ and step increases for $D_{opt}$).

A test for $D_{crit}$ during a $D_{crit}$ search is repeated until predetermined decision criteria have been met (i.e., changes in peak inspiration airflow and/or profile shape features detected by the feature extractor exceed predetermined decision criteria) or until a limit to the $D_{crit}$ search set by the $D_{crit}$ scan is encountered. Each $D_{crit}$ test is initiated with a pre-test period which is followed by a single breath test period and a five breath post-test period. However, when the decision criteria for the $D_{crit}$ search have been satisfied during the single breath test, there is no post-test period.

The $D_{opt}$ search is a series of step increases in displacement (e.g., 0.5 to 2 millimeters) which is initiated after $D_{crit}$ has been determined. The search for $D_{opt}$ involves finding the mandible position at which the peak flow and the flow profile do not improve after a predetermined step increase in displacement. Thus, the minimum effective mandible protruded distance represents that distance at which there is no improvement in the flow profile after a worsening in the flow profile.

Each $D_{opt}$ test is initiated with a pre-test similar to that of a $D_{crit}$ pre-test. A short test period and a longer post-test period follow the pre-test. A $D_{opt}$ search continues provided normal rules of operation are met until predetermined decision criteria for a minimum effective mandible position have been met.

In any test, if the decision criteria for a flow alone condition was exceeded ($D_{crit}$) or not exceeded ($D_{opt}$), then the test is repeated. A flow alone condition corresponds to a relatively large change in peak airflow with little or no relative change in roundness and/or flatness. If an apnea, hypoventilation or respiratory variation error is detected during the testing, the testing mode is exited and the system goes directly to the mandible position of the previous non-testing period.

The decision criteria for $D_{crit}$ are considered to have been satisfied if a relative change in extracted features exceeds the predetermined decision criteria (DC) in any one of four ways: (1) difference between feature values extracted during a first breath test and currently established pre-test feature values exceed the DC; (2) difference between feature values extracted using an average of 4th and 5th breaths detected during the post-test (post-test average) and currently established pre-test feature values exceed the DC; (3) difference between feature values extracted during subsequent single test breaths and the initial pre-test feature values previously established during the initial pre-test exceed the DC; or (4) difference between feature values extracted during subsequent post-tests and feature values of the initial pre-test exceed the DC. The detection of $D_{crit}$ using the comparisons of (3) and (4) above is referred to herein as a trend test. While comparisons similar to (1) and (2) above are used to identify $D_{opt}$, the trend test comparisons are used only to determine $D_{crit}$.

More particularly, the trend test is used exclusively in the $D_{crit}$ search to detect a progressive decrease in the flow profile over the $D_{crit}$ search that may not show up during any one single breath test or post-test. As described above, the trend test uses the initial pre-test features (e.g., five breath average) as the template for subsequent comparisons during tests (3) and (4).

In an exemplary embodiment, a test is true during a $D_{crit}$ search if relative changes in the $V_P$ feature and the flatness feature or relative changes in the $V_P$ feature and the roundness feature have exceeded the DC. Similarly, during a $D_{opt}$ search, if relative changes in the $V_P$ feature and the flatness feature or relative changes in the $V_P$ feature and the roundness feature changes have not exceeded the DC, the test is true.

A search for $D_{crit}$ begins with the scan protocol. As mentioned above, an exemplary scan is an incremental step decrease in mandible displacement. This decrease is preceded by a predetermined period (e.g., 5 breaths). The average values from the features during the pre-step decrease of a scan are used as control values during the scan. If the comparison between the predetermined period average and the post step decrease during a scan is significant, the system records that the scan was significant and the post scan mandible position becomes the limiting position during the $D_{crit}$ search.

The search protocol begins with the search for $D_{crit}$ at the same mandible position as the preceding scan. The search protocol begins with a pre-test during which, for example, 5 breaths prior a step decrease are averaged and used as controls for comparisons during subsequent single breath tests and post-tests. Following the pre-test breaths, the protruded distance is decreased a predetermined incremental step and the subsequent inspiration breath features are collected.

If the breath features after the decrease did not exceed the DC set for this degree of displacement, then the mandible position is left unchanged and a post-test period begins, for example, consisting of 5 breaths. The fourth and fifth breaths of this post-test period are averaged (i.e., post-test average) and the average is tested to see if it exceeded the same DC of the single breath test. If the DC is exceeded in either the single breath test or the post-test average, then the mandible position is returned to the position set during the pre-test period and a $D_{opt}$ search is initiated. When the mandible is protruded during the $D_{opt}$ search, a slightly longer test period (e.g., in the range of 15 to 60 seconds, 5 to 20 breaths) is used.

If neither the single breath test nor the post-test average exceeded the DC, then another test is performed, in this case a $D_{crit}$ test. Accordingly, during a subsequent single breath test and post-test, a trend test will be used to compare extracted features with features of the initial pre-test average. These comparisons are performed in addition to comparisons of extracted features with the current pre-test average as discussed above.

In an exemplary embodiment, if a second cycle of a $D_{crit}$ search pre-test, single breath test, and post-test does not exceed the DC, or if the previous $D_{crit}$ scan was significant but the limiting distance was not reached, then the scan protocol is repeated at the previous search position. This basic scan-search combined protocol is repeated until the least displacement of the mandible is reached or until the comparisons exceed the test criteria. For example, if the initial scan was not significant and $D_{crit}$ has not been detected after two incremental decreases, another scan will be performed. In this scan, an additional decrease is introduced. The aforementioned $D_{crit}$ search is then repeated.

An exemplary search protocol for $D_{opt}$ is slightly different than the search used to identify $D_{crit}$. A scan is not used in the testing protocol to identify $D_{opt}$. Further, during a preferred $D_{opt}$ search, a pre-test series, for example, of 5 breaths, precedes an incremental increase in mandible displacement. Further, the trend tests used to identify $D_{crit}$ are not used to identify $D_{opt}$. The $D_{opt}$ search protocol consists of, for example, 5 pre-test breaths, a step increase in displacement, and an optional post-test period (e.g., in the range of 15 to 60 seconds) if it was the first $D_{opt}$ test. This $D_{opt}$ protocol is repeated until no significant differences exist between $V_p$ and/or profile shape indices of the pre-test relative to the single breath test and the post-test.

d. Long Term Memory

The long term memory stores specific information for use by the physician or a sleep laboratory for diagnostic or for follow-up therapeutic applications. In addition to recording upper airway system characteristic features during system operation, stored information can be assembled to identify the patient's use of the auto-MP system at home or in diagnostic or therapeutic studies. This information can be used by the physician to assess the integrity of results obtained during home or lab use of the system.

It will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A method for adaptively controlling mandibular displacement for a treatment of obstructive sleep apnea in a patient, comprising:
   (a) monitoring the patient for evidence of obstruction of the patient's airway;
   (b) displacing the patient's mandible by applying external force to the patient's jaw or teeth if evidence of obstruction is detected; and
   (c) repeating steps (a) and (b) until evidence of obstruction is eliminated or reduced below a predetermined value.

2. The method of claim 1 wherein the patient's mandible is displaced a predetermined increment.

3. The method of claim 2 wherein the patient is monitored for a time in a range of 10 seconds to 4 minutes after the mandible has been displaced.

4. The method of claim 2 wherein the patient is monitored for a time in a range of 2 to 4 minutes after the mandible has been displaced.

5. The method of claim 2 wherein the increment is in a range of 0.25 to 2 millimeters.

6. The method of claim 2 wherein the increment is in a range of 0.5 to 1 millimeter.

7. The method of claim 1 further comprising:
   detecting airflow in the patient's airway;
   averaging said airflow information over a predetermined period; and
   comparing the airflow in the patient's airway during a first test period after the mandible is displaced to the averaged airflow information to determined if evidence of obstruction is above the predetermined value.

8. The method of claim 7 wherein the predetermined period is in a range of 2 to 10 breaths.

9. The method of claim 7 wherein the predetermined period is in a range of 3 to 5 breaths.

10. The method of claim 1 further comprising:
    detecting airflow in the patient's airway in predetermined increments of time;
    identifying periods of inspiration and expiration;
    extracting features of the patient's airway during at least one of said periods of inspiration;
    identifying airflow profiles based on said detected airflow and said extracted features;
    determining a first mandible displacement which produces a first predetermined airflow profile;
    introducing incremental mandible displacements to determine a second mandible displacement which produces a second predetermined airflow profile; and
    setting the patient's mandible at the second mandible displacement.

11. The method of claim 10, wherein the extracting step further includes a step of:
    determining an inspiration airflow profile for the period of inspiration.

12. A method for adaptively controlling mandibular displacement for a treatment of obstructive sleep apnea in a patient, comprising the steps of:
    detecting airflow in the patient's airway in predetermined increments of time;
    identifying periods of inspiration and expiration;
    extracting features of the patient's airway during at least one of said periods of inspiration wherein the extracting includes determining an inspiration airflow profile for the period of inspiration;
    identifying airflow profiles based on said detected airflow and said extracted features;
    (a) monitoring the patient for evidence of an obstruction of the patient's airway;
    (b) displacing the patient's mandible if evidence of the obstruction is detected by determining a first mandible displacement which produces a first predetermined airflow profile; and
    (c) repeating steps (a) and (b) by introducing incremental mandible displacements to determine a second mandible displacement which produces a second predetermined airflow profile and setting the patient's mandible at the second mandible displacement until evidence of the obstruction is eliminated or reduced below a predetermined value, wherein the step of determining an inspiration airflow profile further includes the step of:

calculating a roundness feature and a flatness feature for the period of inspiration.

13. A method for adaptively controlling mandibular displacement for a treatment of obstructive sleep apnea in a patient, comprising the steps of:

detecting an obstruction in a patient's upper airway system;

identifying periods of inspiration and expiration for the patient; and incrementally adjusting a patient's mandible by applying external force to the patient's jaw or teeth in response to the obstruction information detected during the period of inspiration.

14. The method of claim 13, wherein the step of adjusting further includes the steps of:

identifying a mandibular position at which a significant obstruction occurs during said inspiration; and identifying an optimum mandibular position for eliminating said obstruction during said inspiration.

15. The method of claim 14, wherein said steps of identifying the mandibular position and the optimum mandibular position further includes the step of:

introducing incremental mandibular displacements;

extracting characteristic features of said upper airway system during inspiration;

using said extracted characteristics to identify the optimum mandibular position and the mandibular position at which the significant obstruction occurs.

16. The method of claim 13, wherein the step of adjusting is performed by identifying relative changes in airflow during said step of detecting.

17. The method of claim 13, wherein the step of adjusting further includes the steps of:

extracting features indicative of airflow resistance in said upper airway system.

18. A system for adaptively controlling mandibular displacement for the treatment of obstructive sleep apnea in a patient, comprising:

an adjustable mandibular displacement device which applies external force to the patient's jaw or teeth;

a unit which detects evidence of obstruction of the patient's airway; and a control system for adaptively controlling the adjustable mandibular displacement device in response to the detecting unit.

19. The system of claim 18 wherein the adjustable mandibular displacement device comprises:

an upper dental appliance;

a lower dental appliance having a mounting bracket extending therefrom; and an actuator attached to the mounting bracket and in contact with the upper dental appliance.

20. The system of claim 18 wherein the detecting unit comprises an oxygen saturation monitor.

21. The system of claim 18 wherein the detecting unit comprises a sound monitor.

22. The system of claim 18 wherein the detecting unit comprises an airflow monitor.

* * * * *